United States Patent
Dean et al.

(10) Patent No.: US 10,765,884 B1
(45) Date of Patent: Sep. 8, 2020

(54) METHODS TO TRIGGER HIGH AMPLITUDE OSCILLATIONS OR RESONANCE IN THE CARDIOVASCULAR SYSTEM OF A PATIENT USING ELECTROMAGNETIC STIMULATION

(71) Applicants: Steven G Dean, New York, NY (US); Frederick Muench, Brooklyn, NY (US)

(72) Inventors: Steven G Dean, New York, NY (US); Frederick Muench, Brooklyn, NY (US)

( * ) Notice: Subject to any disclaimer, the term of this patent is extended or adjusted under 35 U.S.C. 154(b) by 1556 days.

(21) Appl. No.: 14/608,154

(22) Filed: Jan. 28, 2015

Related U.S. Application Data

(63) Continuation-in-part of application No. 13/779,613, filed on Feb. 27, 2013, now Pat. No. 9,943,461, and a continuation-in-part of application No. 14/198,312, filed on Mar. 5, 2014, now Pat. No. 10,098,810.

(60) Provisional application No. 61/933,250, filed on Jan. 29, 2014, provisional application No. 61/933,255, filed on Jan. 29, 2014.

(51) Int. Cl.
*A61N 5/06* (2006.01)

(52) U.S. Cl.
CPC .... *A61N 5/0613* (2013.01); *A61N 2005/0626* (2013.01); *A61N 2005/0662* (2013.01)

(58) Field of Classification Search
CPC .......... A61N 5/0613; A61N 2005/0626; A61N 2005/0662

USPC .......................................................... 607/88
See application file for complete search history.

(56) References Cited

U.S. PATENT DOCUMENTS

| | | |
|---|---|---|
| 4,315,502 A | 2/1982 | Gorges |
| 6,299,632 B1 | 10/2001 | Jaillet |
| 6,662,032 B1 | 12/2003 | Gavish et al. |
| 7,311,658 B2 | 12/2007 | Elliot |
| 7,643,875 B2 | 1/2010 | Heil et al. |
| 8,219,188 B2 | 7/2012 | Graig |
| 8,442,632 B2 | 5/2013 | Kullock et al. |

FOREIGN PATENT DOCUMENTS

| | | |
|---|---|---|
| WO | WO 2008/131553 | 4/2007 |
| WO | WO 2010/047834 | 10/2008 |
| WO | WO 2014/170880 | 4/2014 |

OTHER PUBLICATIONS

U.S. Appl. No. 14/198,312, Muench, et al., filed Mar. 5, 2014.

(Continued)

*Primary Examiner* — Aaron F Roane
(74) *Attorney, Agent, or Firm* — Byrne Poh LLP

(57) ABSTRACT

Various embodiments of and methods for providing therapeutic light or electromagnetic radiation stimulation to a patient are disclosed and described. Therapeutic light stimulation is provided to a patient through a light source, and is configured to trigger or induce resonance or high amplitude oscillations in a cardiovascular system of the patient. Inducing such oscillations or resonance can aid in training autonomic reflexes and improve their functioning.

20 Claims, 5 Drawing Sheets

(56) References Cited

OTHER PUBLICATIONS

Doucet, B.M., et al., Neuromuscular Electrical Stimulation for Skeletal Muscle Function, Yale Jrnl. of Biology and Medicine 85 (2012), pp. 201-215.
Alpha-Stim Aid and You, , brochure c. 2014 by Electromedical Products Int'l Inc.
Grote, V., et al. , Cardio-autonomic Control and Wellbeing Due to Oscillating Color Light Exposure, Physiology & Behavior 114-115 (2013) 55-64.
Hashmi, J.T., et al., Effect of Pulsing in Low-Level Light Therapy, Lasers Surg Med. Aug. 2010; 42(6): 450-466.

METHODS TO TRIGGER HIGH AMPLITUDE OSCILLATIONS OR RESONANCE IN THE CARDIOVASCULAR SYSTEM OF A PATIENT USING ELECTROMAGNETIC STIMULATION

RELATED APPLICATIONS

This application claims priority and other benefits from: (a) U.S. Provisional Patent Application Ser. No. 61/933,250 entitled "Electrical Stimulation to Trigger High Amplitude Oscillations or Resonance in the Cardiovascular System of a Patient" to Dean et al. filed on Jan. 29, 2014 (hereafter "the '250 patent application"), and (b) U.S. Provisional Patent Application Ser. No. 61/933,255 entitled "Manipulating Electromagnetic Radiation to Trigger High Amplitude Oscillations or Resonance in the Cardiovascular System" to Dean et al. filed on Jan. 29, 2014 (hereafter "the '255 patent application").

This application also claims priority and other benefits from, and is a continuation-in-part of each of: (c) U.S. Utility patent application Ser. No. 13/779,613 entitled "Systems, Devices, Components and Methods for Triggering or Inducing Resonance or High Amplitude Oscillations in a Cardiovascular System of a Patient" to Muench et al. filed on Feb. 27, 2013 (hereafter "the '613 patent application), and (d) U.S. Utility patent application Ser. No. 14/198,312 entitled "Systems, Devices, Components and Methods for Triggering or Inducing Resonance or High Amplitude Oscillations in a Cardiovascular System of a Patient" to Muench et al. filed on Mar. 5, 2014 (hereafter "the '312 patent application").

Each of the foregoing four patent applications, namely the '250 patent application, the '255 patent application, the '613 patent application, and the '312 patent application, is hereby incorporated by reference herein, each in its respective entirety. This application also incorporates by reference herein the entirety of U.S. patent application Ser. No. 14/608,109, entitled "Methods to Trigger High Amplitude Oscillations or Resonance in the Cardiovascular System of a Patient Using Electrical Stimulation" to Steven G. Dean et al., filed on Jan. 28, 2015.

FIELD OF THE INVENTION

Various embodiments of the invention described herein relate to the field of methods, systems, devices and components for delivering external light or electromagnetic stimulation therapy to a patient to induce or trigger high amplitude oscillations or resonance in the cardiovascular system of a patient.

BACKGROUND

Low or reduced baroreflex sensitivity in patients is associated with numerous problems and disorders (e.g., hypertension, congestive heart failure, coronary heart disease, hypertension, depression, alcohol or drug use disorders and aging). Reduced baroreflex sensitivity in patients blunts the flexibility of the body's self-regulatory system. Contrariwise, high baroreflex sensitivity in patients is generally associated with health and wellness.

What is needed, therefore, are efficacious and cost effective means and methods for increasing baroreflex sensitivity in patients.

Various printed publications, patents and patent applications containing subject matter relating directly or indirectly to the methods, systems, devices and components described below include, but are not limited to, the following:

Vaschillo, E. G., Vaschillo, B., Lehrer, P. M. Characteristics of Resonance in Heart Rate Variability Stimulated by Biofeedback. Applied Psychophysiology and Biofeedback. 2006, June; 31(2): 129-142

Vaschillo, E G, Vaschillo, B, Buckman, J F, Pandina, R J, and Bates, M E. The Investigation and Clinical Significance of Resonance in the Heart Rate and Vascular Tone Baroreflexes. In BIOSTEC 2010, CCIS 127, A. Fred, J. Filipe, and H. Gamboa (Eds.), pp. 224-237, Springer, Heidelberg.

Vaschillo, E. G., Bates, M, Vaschillo, B., Lehrer, P. M., et al. Heart rate variability response to alcohol, placebo, and emotional picture cue challenges: Effects of 0.1-Hz stimulation, Psychophysiology, 45 (2008), 847-858.

France C R, France J L, Patterson S M. Blood pressure and cerebral oxygenation responses to skeletal muscle tension: a comparison of two physical maneuvers to prevent vasovagal reactions. Clinical Physiology and Functional Imaging. 2006; 26:21-25.

Vaschillo, E. G., Bates, M. E., Vaschillo, B., Lehrer, P., Udo, Lehrer P, Vaschillo E, Trost Z, France C. Effects of rhythmical muscle tension at 0.1 Hz on cardiovascular resonance and the baroreflex. Biological Psychology. 2009; 81:24-30.

Wheat, A. & Larkin, K. Biofeedback of Heart Rate Variability and Related Physiology: A Critical Review Applied Psychophysiology and Biofeedback. 2010, 35: 3: 229-242.

Hashmi et al. Effect of Pulsing in Low-Level Light Therapy, Lasers Surg Med. 2010; 42(6): 450-466.

Vaschillo, E. G., Vaschillo, B., Pandina, R. J. and Bates, M. E. (2011), Resonances in the cardiovascular system caused by rhythmical muscle tension. Psychophysiology, 48: 927-936.

Grote et al. Cardio-autonomic control and wellbeing due to oscillating color light exposure, Physiology & Behavior 114-115 (2013) 55-64.

U.S. Pat. No. 4,315,502 to Gorges for "Learning relaxation device," Oct. 11, 1979.

U.S. Pat. No. 8,442,632 to Kullock et al. for "Method and apparatus for affecting the autonomic nervous system," Oct. 21, 1998.

U.S. Pat. No. 6,299,632 to Jalliet for "Method for changing critical brain activity using light and sound," Nov. 30, 1998.

U.S. Pat. No. 6,662,032 to Gavish et al. for "Interventive-diagnostic device," Jul. 6, 1999.

U.S. Pat. No. 5,997,482 to Vaschillo et al. for "Therapeutic method for a human subject," Dec. 7, 1999.

U.S. Pat. No. 7,311,658 to Elliot for "Method and system providing a fundamental musical interval for heart rate variability synchronization," Mar. 25, 2004.

U.S. Pat. No. 7,117,032 to Childre et al. for "Systems and methods for facilitating physiological coherence using respiration training," Oct. 3, 2006.

WO Patent No. 2008131553 to Martel for "Light modulation device and system," Apr. 30, 2007.

WO Application No. 2014170880 to Nissila et al. for "Light therapy apparatus and method," Apr. 18, 2014.

The dates of the foregoing publications may correspond to any one of priority dates, filing dates, publication dates, issue dates and retrieval dates. Listing of the above patents and patent applications in this background section is not, and shall not be construed as, an admission by the applicants or their counsel that one or more publications from the above list constitutes prior art in respect of the applicant's various inventions.

Upon having read and understood the Summary, Detailed Descriptions and Claims set forth below, those skilled in the art will appreciate that at least some of the methods, systems, devices and components disclosed in the printed publications listed herein may be modified advantageously in accordance with the teachings of the various embodiments that are disclosed and described herein.

SUMMARY

Resonance or high amplitude oscillations can be induced or created in the cardiovascular system (CVS) by providing electromagnetic stimulation therapy within the light range at specific frequencies either close to or according to a patient's CVS heart rate (HR) resonant frequency.

Disclosed and described herein are techniques for entraining frequencies in the CVS using a form of noninvasive light stimulation wherein noninvasive refers to any form of light stimulation delivered to an individual. Examples of such light stimulation regimes for the HR baroreflex system include an 8-14 second cycle (e.g., on for 4-7 seconds and off for 4-7 seconds, or increasing in light stimulation frequency for 4-7 seconds and decreasing in light stimulation frequency for 4-7 seconds) at stable electromagnetic wavelengths. In one embodiment, there is provided a method of providing light stimulation therapy to a patient comprising delivering the at least one light stimulation signal being successively delivered to the patient over first periods of time and not being delivered to the patient over second periods of time, the second periods of time being interposed between the first periods of time; wherein the at least one light stimulation signal and the first and second periods of time are together configured to trigger or induce resonance or high amplitude oscillations in a cardiovascular system of the patient.

In another embodiment, there is provided a method of providing light stimulation therapy to a patient comprising delivering first and second light stimulation signals, the first and second light stimulation signals corresponding to first and second light stimulation modes, respectively, the first light stimulation mode and first light stimulation signal corresponding to first periods of time, the second light stimulation mode and second light stimulation signal corresponding to second periods of time, the second periods of time being interposed between the first periods of time, the first light stimulation signal being different from the second light stimulation signal, wherein the first and second light stimulation signals, first and second light stimulation modes, and first and second periods of time are together configured to trigger or induce resonance or high amplitude oscillations in a cardiovascular system of the patient.

Further embodiments are disclosed herein including triggering stimulation cycles based on the heart rate resonant frequency of an individual (e.g. between approximately 0.08-0.12 Hz) and vascular tone resonant frequency (e.g. between approximately 0.02-0.04 Hz) or will become apparent to those skilled in the art after having read and understood the specification and drawings hereof.

BRIEF DESCRIPTION OF THE DRAWINGS

Different aspects of the various embodiments will become apparent from the following specification, drawings and claims in which:

The drawings are not necessarily to scale. Like numbers refer to like parts or steps throughout the drawings.

DETAILED DESCRIPTIONS OF SOME EMBODIMENTS

Figure 1:
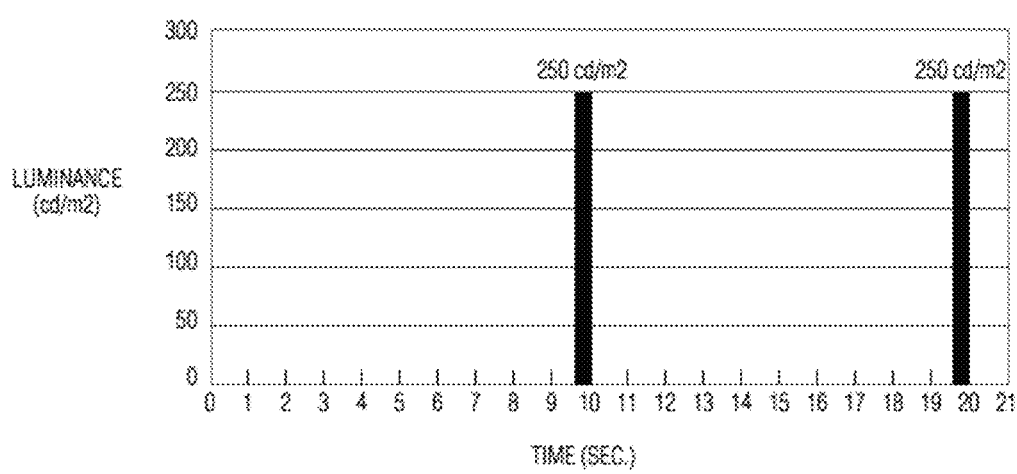
FIGS. 1 and 2 illustrate various embodiments of electromagnetic stimulation regimes and corresponding methods that can be used to provide therapy to a patient.

Described herein are various embodiments of external electromagnetic or light stimulation methods, systems, devices and components that are configured to trigger or induce resonance or high amplitude oscillations in a cardiovascular system of the patient.

According to some embodiments, rhythmical stimulation of the cardiovascular system (CVS) is induced or generated by using electromagnetic radiation or light stimulation to elicit higher than resting amplitude oscillations or resonance in cardiovascular functions (e.g. in heart rate, blood pressure, and vascular tone). Oscillations in these functions train (or exercise) cardiovascular reflexes, including the baroreflex, to improve CVS functioning as well as to promote appropriate adaptive responses to internal and environmental perturbations.

The arterial baroreflex system (BRS) is a reflexive control system that counteracts acute shifts in blood pressure (BP) by invoking compensatory reactions in cardiovascular functions (e.g., heart rate (HR), vascular tone (VT), and stroke volume (SV). Baroreceptors trigger simultaneous reflexive reactions in HR, VT, and SV. The BRS regulates short-term BP serving to protect the brain from stroke and the heart from myocardial infarction as well as to restore its inhibition-excitation balance. Low or reduced baroreflex sensitivity is often associated with numerous problems and disorders, such as hypertension, congestive heart failure, coronary heart disease, depression and aging. Reduced baroreflex sensitivity blunts the flexibility of the regulatory system, whereas a high sensitivity is associated with health and wellness.

Similar to engineering closed loop control systems with delays, the closed loop baroreflex system has been discovered to possess resonance properties. That is, there are certain frequencies (known as resonant or resonance frequencies) at which stimulation of the baroreflex system can elicit high amplitude oscillations in HR, BP, SV, and/or VT. The value of the delay in the feedback control system can be used to define one or more resonant frequencies in the closed loop control system. In one such embodiment, the period of the resonant oscillations is equal to the value of two delays. In a closed loop baroreflex system, periodic driving forces at one or more resonant frequencies can produce much larger amplitudes. This is because a baroreflex system is characterized by delays between changes in BP and HR (~5 seconds), (i.e., periods of resonance oscillation are ~10 s). Each person's baroreflex system has own delays and accordingly own resonance frequencies. These changes can coincide in some fashion with, or can be proportional to, certain resonant frequencies.

Interventions such as slow meditative breathing and progressive muscle relaxation performed at or near a patient's resonant frequency can increase oscillations at these frequencies and increase short-term HR baroreflex sensitivity, vagal tone, and/or heart rate variability. This is especially so in healthy individuals and in patients who suffer from cardiovascular or autonomic nervous system disorders. Like many systems, the cardiovascular system has many different functions, and is characterized by several distinct resonant frequencies.

The baroreflex system is characterized by delays between changes in BP and HR (~5 seconds), as well as between BP and VT (~10-15 seconds), and can have, by way of example, resonant frequencies of ~0.1 Hz and ~0.03 Hz (i.e., periods of resonance oscillation are ~10 seconds (HR resonance) and ~30 seconds (VT resonance). In an HR baroreflex closed-loop system, a shift in BP can cause a compensatory HR response that is delayed for approximately 5 seconds. These delays of approximately 5 seconds can in turn coincide with resonance oscillations of about 0.1 Hz (since oscillation periods are equal to twice the value of the delay—e.g., a cycle of about 10 seconds). The HR baroreflex system in humans can demonstrate resonance properties at frequencies of about 0.1 Hz. Similarly, the VT baroreflex system in humans can demonstrate resonance properties at frequencies of about 0.03 Hz. In a VT baroreflex closed loop system, the compensatory response of the vasculature is delayed for approximately 10-20 seconds as compared to approximately 5 seconds in the HR baroreflex system. This delay of about 15 seconds coincides with resonance oscillations of about 0.03 Hz (since, again, oscillation periods are equal to twice the value of the delay, e.g., a cycle of about 30 seconds comprised of adjacent 15 second periods).

One mechanism to create or induce resonance in an HR baroreflex system has been through slow paced breathing at an average of about 6 full cycles per minute in which an individual inhales for approximately 4-7 seconds and exhales for approximately 4-7 seconds. Doing so results in individual inhalation-exhalation cycles of about 8-14 seconds. While rates vary according to the individual, breathing at such rates can produce high amplitude oscillations in the HR baroreflex system that typically range between about 0.075 Hz and about 0.125 Hz, depending on short-term baroreflex sensitivity and short-term heart rate variability. Long-term practice of such breathing patterns has been linked to an increase in baroreflex sensitivity and heart rate variability (HRV) at rest. In other words, it is possible to cause or induce resonance in the CVS through manipulation of breathing, auditory and visual stimuli, or rhythmical muscle relaxation.

One mechanism to induce resonance in the VT baroreflex system has also been through slow paced breathing at an average of approximately 2-3 full cycles per minute in which an individual inhales for approximately 10-20 seconds and exhales for approximately 10-20 seconds resulting in individual inhalation-exhalation cycles of 20-40 seconds. While rates vary according to the individual, breathing at such rates can produce high amplitude oscillations in the VT baroreflex system of about 0.03 Hz, depending among other things on normalization in vascular tone and blood pressure regulation. Similar to the HR baroreflex system, it is possible to cause resonance in the VT baroreflex system through the manipulation of breathing.

Research directed to the effects of breathing at approximately the foregoing rates has revealed significant potential effects on the CVS, with potential cascading effects on disorders associated with vagal and autonomic dysfunction. Some studies have revealed that paced breathing at a rate of approximately 0.1 Hz can be used effectively in heart rate variability (HRV) biofeedback techniques, as described by Lehrer and Vaschillo (2003). Some studies have also revealed that entraining the CVS and breathing at about 0.1 hz can improve the symptoms of numerous disorders, such as depression, PTSD, fibromyalgia, hypertension, abdominal pain, and coronary heart disease (Vaschillo et al., 2010; Wheat and Larkin, 2010). As noted by Vaschillo and colleagues in 2010, "the therapeutic effects of HRV biofeedback are thought to be due to the induction of high-amplitude oscillations in HR, and VT at specific frequencies which exercise and activate homeostatic reflexes (e.g., the baroreflex reflex), retrain them, and initiate, through the baroreceptors, a cascade of neurobiological events that produces a generalized inhibitory effect on the brain."

Other methods to cause high amplitude oscillation in HR, BP, and VT at specific frequencies may also be possible, such as presenting emotional pictures to a patient (e.g., 5 seconds with pictures, 5 seconds without pictures—see Vaschillo et al., 2010), and self-induced rhythmical muscle tension stimulation at the same frequency (France et al., 2006; Lehrer et al., 2009). External or patient-induced stimulation provided at specific frequencies may thus entrain similar frequencies in the CVS through increasing spectral power in the interbeat interval (RRI), blood pressure (BP) and pulse transit time (PTT).

According to some embodiments, external manipulation at specific light frequencies is used to cause mirrored or closed to mirrored oscillations in the CVS system to improve health and wellbeing. The light stimulation frequency or range of frequencies is selected to cause a mirrored shift in the frequency of CVS rhythms. External stimulation via manipulations of visible and non-visible light stimulation can also entrain the CVS to increase oscillations at specific frequencies. This can have profound implications for the treatment of numerous psychiatric and medical disorders, particularly depression and cardiovascular disease, which are often associated with dysregulation in the cardiovascular system. As indicated in our previous application using vibration (U.S. patent application Ser. No. 13/779,613), such methods can induce resonance or high amplitude oscillations passively rather than requiring active involvement from the patient (e.g., paced breathing or muscle tension). According to one embodiment, there is provided a passive means to stimulate the same reflexes using light, which can extend the therapeutic effects to a significantly larger population in need.

Light includes electromagnetic radiation ranging in wavelength between about 10 nanometers (nm) and about 1 millimeter (mm). The light spectrum includes ultraviolet radiation (10 nm to 400 nm), visible light (400 to about 700 nm), and infrared radiation (700 nm to 1 mm). According to several embodiments, electromagnetic radiation wavelengths from the ultraviolet to infrared radiation spectra may be employed, such as between about 10 nm to about 1 mm, including visible light.

According to various embodiments, light therapy may be provided to treat depression and other physical and mental health problems, where electromagnetic radiation having wavelengths between about 10 nm and 1 mm is employed. Such therapies may be provided while focusing on a specific range of wavelengths or intensity of the delivered light. The cycle or manner in which the light is delivered is important. Various embodiments employ cycles of on-off of light provided at stable or substantially uniform light wavelengths rather than shifting wavelengths. In one embodiment, cycles of on-off light stimulation (e.g., on for 5 seconds-off for 5 seconds at any suitable LUX or wavelength) are employed to stimulate the baroreflexes and create resonance or high amplitude oscillations in the cardiovascular system of a patient. One mechanism of action to provide therapy to a patient is to stimulate baroreflexes by providing cycles of on-off light, or by providing cycles of increasing-decreasing light luminosity or intensity over a cycle having a duration of, e.g., 10 seconds. Substantially uniform wavelengths of light are provided during the cycle while the level or intensity of light provided can be modulated or changed.

Disclosed and described herein are techniques for entraining frequencies in the CVS using light radiation, with special emphasis on visible light wavelengths and alterations in visible light to promote human adaptability and responsiveness to internal and environmental perturbations, as well as to promote overall health and wellbeing. Rhythmical external stimulation of the CVS at specific frequencies can be employed to affect the CVS. The high amplitude oscillation of cardiovascular functions at resonant frequencies generated by such stimulation can help regulate the CVS, modulate the vagus nerve and the brain, and normalize the inhibition-excitation balance of the CVS on brain systems, and in such a manner provide beneficial therapy to a patient.

According to various embodiments, resonance or high amplitude oscillations are induced or generated in the CVS of a person using specific on-off periods of light or electromagnetic stimulation or by increasing-decreasing periods of visible light stimulation at varying intensities over a predetermined period of time. The resonance or high amplitude oscillations can be induced or created in the CVS by means of a system or device that creates and/or delivers electromagnetic or light stimulation to a patient with the stimulation signal being successively delivered to the patient over first periods of time (or increasing over the first period of time) and not being delivered to the patient over second periods of time (or decreasing over the second period of time), the second periods of time being interposed between the first periods of time; wherein the at least one stimulation signal and the first and second periods of time are together configured to trigger a third period or total cycle designed to induce resonance or high amplitude oscillations in a cardiovascular system of the patient. The third period created by the interposed first and second periods can range between about 8 and 40 seconds, between about 20 and 40 seconds, between about 20 and 30 seconds, between about 26 and 34 seconds, between about 8 and 14 seconds, between about 8 and 12 seconds, and/or between about 9 and 11 seconds. The first period can range between about 100 milliseconds and 19.9 seconds and the second period can range between about 100 milliseconds and 19.9 seconds, which are together configured to create the third period.

According to various embodiments, the foregoing described third periods are repeated consecutively to induce resonance in the cardiovascular system of a patient over a period of time determined to be effective for a given patient, which, by way of non-limiting example, may range between about 5 cycles and 50,000 cycles, or between about 1 minute and 10 hours.

According to some embodiments, two basic forms or embodiments of light stimulation are provided.

In a first embodiment, the third period or cycle created by the interposed first and second periods ranges between about 8 and 40 seconds, between about 20 and 40 seconds, between about 20 and 30 seconds, between about 26 and 34 seconds, between about 8 and 14 seconds, between about 8 and 12 seconds, and/or between about 9 and 11 seconds in duration, the light stimulation is "on" for the first period and not on or off for the second period, and wherein the light signals of the first and second periods of time are together configured to create the third period, which triggers or induces resonance or high amplitude oscillations in a cardiovascular system of the patient. Both the first and second periods can be active or inactive for any period of time within the third period or total cycle. For example, if the third period is a 10 second cycle, the first on period can be where light is "on" for 5 seconds and the second light "off" period can be for 5 seconds. Alternatively, a 10 second third period can also comprise a first period of "on" light stimulation 500 milliseconds in duration, and a second period of no or "off" light stimulation for 9500 milliseconds in duration (see FIG. 1) or a first period of on stimulation for 1 second and a second period of no or "off" light for 9 seconds and so on. Resonance or high amplitude oscillations of the CVS are induced or generated by the third period or total cycle of on-off light stimulation, where the first and second periods can each be varied by any suitable amount of time within the third period.

In a second embodiment, the third period or cycle created by the interposed first and second periods ranges between about 8 and 40 seconds, between about 20 and 40 seconds, between about 20 and 30 seconds, between about 26 and 34 seconds, between about 8 and 14 seconds, between about 8 and 12 seconds, and/or between about 9 and 11 seconds in duration, where the light stimulation is increasing in intensity over the first period and decreasing in intensity over the second period, and where the light signals within the first and second periods of time are together configured to create the third period to trigger or induce resonance or high amplitude oscillations in a cardiovascular system of the patient. Both the first and second periods may be increasing or decreasing in intensity or amplitude for any period of time within the third period or total cycle. For example, if the third period is a 10 second cycle, the first increasing period of light intensity can be for 5 seconds and the second decreasing period of light intensity can be for 5 seconds. Alternatively, a 10 second third period can also comprise a first increasing light stimulation intensity period of about 100 milliseconds and a second decreasing light stimulation intensity period of about 9900 milliseconds, or a first increasing light stimulation intensity period for about 1 second and a second decreasing light stimulation intensity period of 9 seconds, and so on. Resonance or high amplitude oscillations of the CVS are induced or generated by the third period/total cycle of increasing-decreasing stimulation wherein the first and second periods can each be any amount of time within the third period.

According to various embodiments, a light therapy source or a passive light source is employed to deliver light stimulation therapy to a patient using the on-off and increasing-decreasing patterns described above, and which may be configured to be on at any stable or substantially uniform wavelength, frequency or intensity during the first period, and off or substantially off with no stimulation for the second period, where the light signals within the first and second periods of time are together configured to create the third period. The various embodiments contemplate the use of suitable forms of light radiation wavelengths, including visible light (wavelengths between about 380 nm and about 700 nm), light not visible to the human eye such as ultraviolet light (wavelengths between about 10 nm and about 380 nm), and infrared light (wavelengths between about 700 nm and about 1 mm), and suitable frequencies or intensities falling within such light spectra.

Figure 3:
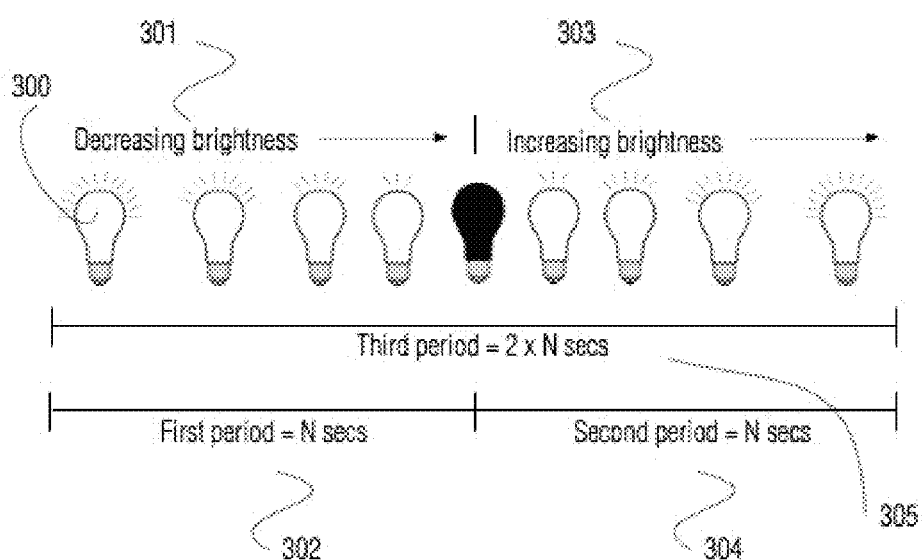
FIGS. 3 through 5 illustrate various embodiments of embodiments of systems and devices 300, 400, 500 for delivering therapeutic electromagnetic stimulation to a patient.

FIG. 3 shows one embodiment of providing therapeutic light or light stimulation to a patient using a light source such as a light bulb 300. In FIG. 3, second third period 305 features decreasing brightness 301 of light bulb 300 over first period of N seconds 302 followed by increasing brightness 303 of light bulb 300 over second period of N seconds 304, and then repeating such pattern of light stimulation.

Figure 4:
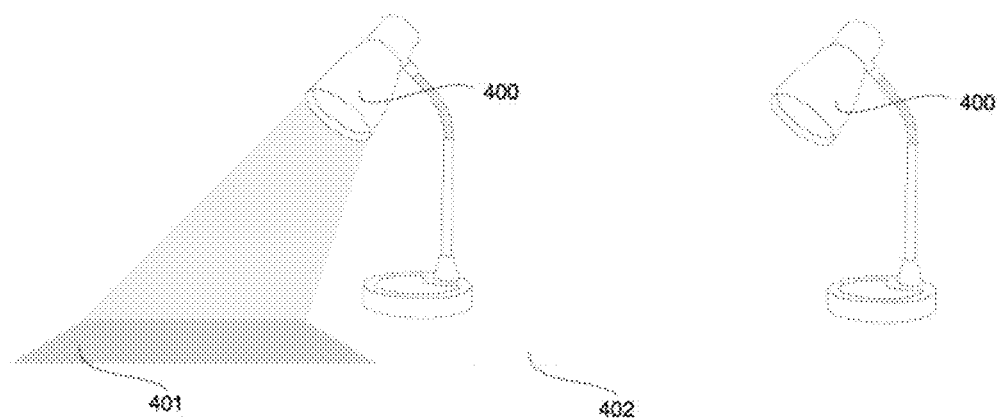

FIG. 4 shows another embodiment of providing therapeutic light or light stimulation using light source 400 that is on 401 for the first period and off 402 for the second period.

Figure 5:
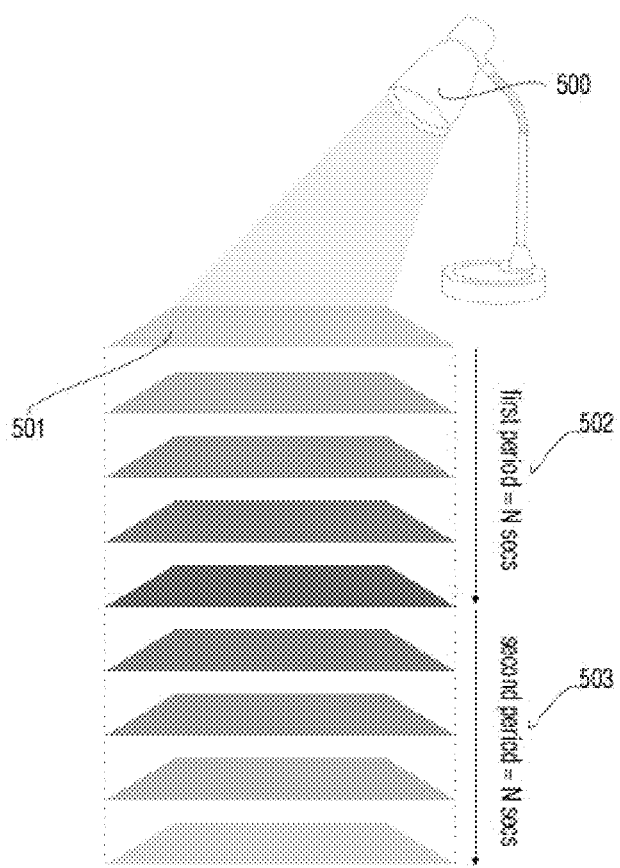

FIG. 5 another embodiment of providing therapeutic light or light stimulation using light source 500 on a surface 501 decreasing in intensity for the first period 502 and increasing in intensity over the second period 503.

Figure 2:
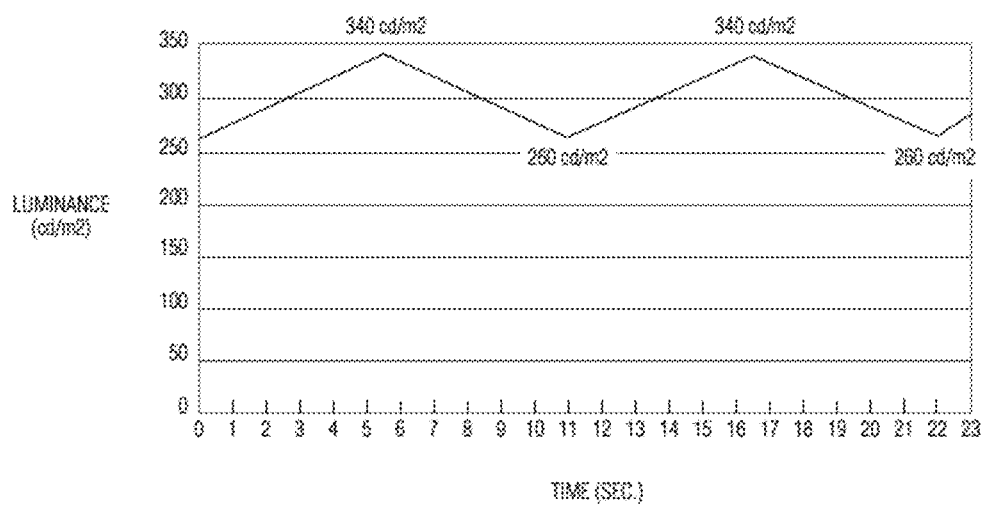

The various embodiments include within their scope providing stable or substantially uniform wavelengths of suitable light radiation or light as measured according to any of a number of different light units, such as luminous flux [lumens (lm)], luminous intensity [Candela (cd)], illuminance [Lux (lx)], and luminance [candela per square meter (cd/m2)]. Using luminance as one example, a computer display having a brightness display of 260 cd/m2 (candela per square meter) can be configured to increase in brightness slowly over 5.5 seconds to peak at 340 cd/m2 and then slowly decrease in brightness for 5.5 seconds back to 260 cd/m2, and so on, creating a repeating 11 second total cycle of increasing and decreasing luminance from 260 cd/m2/to 340 cd/m2 with a second period of time interposed between a first period of time to create a total cycle or third period of 11 seconds (see FIG. 2). The increasing or decreasing amount of light is a repeating cycle, and according to some embodiments it does not matter whether the increasing or decreasing light phase falls within the first period or the second period. In another example, luminance from any light source may be "on" at 250 cd/m2 for 500 ms seconds then "off" with no light source or 0.0 cd/m2 for 9500 ms creating a repeating 10 second total cycle of on-off luminance with the second period of time interposed between the first period of time to create a total cycle or third period of 10 seconds (FIG. 1). Other cycles are obviously contemplated, such as "on" for 100 milliseconds and "off" for 9.9 seconds, or increasing the candelas provided per square meter for 15 seconds and decreasing the candelas provided per square meter for 15 seconds. See, for example, FIGS. 3 through 5. Changes in light stimulation can be achieved using any suitable method or device capable of configuring visible or non-visible light to create appropriate repeating cycles of first, second and third periods as described above, with the primary third period cycles inducing or generating HR and VT resonance for suitable periods of time such as between about 8 and 12 seconds, or between about 20 and 40 seconds. However, since each resonant frequency can be different for different individuals, different stimulation cycles are contemplated for different individuals within, by way of non-limiting example, third periods ranging between about 8 and 40 seconds in duration.

In addition, changes in light or light radiation wavelength or intensity to induce resonance can be achieved using any suitable method or device configured to alter the light source to change or adjust light output power or RMS voltage (such as a dimmer switch), wattage, diffusion, collimation, focusing lenses, concave/convex mirrors, prisms, and so on.

While some embodiments employ visible light stimulation, other embodiments employ the non-visible wavelengths described above. Devices that emit visible or non-visible light, such as mobile phones, computers, tablets, televisions, LEDs, LCDs, incandescent light sources can be configured for use in the various embodiments. Suitable sources of visible and/or non-visible light include, but are not limited to, lamps, chemiluminescence light sources (lightsticks), fluorescent lights, phosphorescent lights, electron-stimulated lights, cathodoluminescence lights, electron stimulated luminescence lights (e.g., ESL light bulbs), incandescent lamps, carbon button lamps, conventional incandescent light bulbs, flashlights, halogen lamps, globars, Ernst lamps, electroluminescent lights, light-emitting diodes, organic light-emitting diodes, polymer light-emitting diodes, solid-state lighting, LED and LCD lamps, light-emitting electrochemical cells (LECs), electroluminescent sheets, electroluminescent wires, gas discharge lamps fluorescent lamps, compact fluorescent lamps, tanning lamps, black lights, hollow cathode lamps, excimer lamps, neon and argon lamps, dekatron lights, nixie tube lights, plasma lamps, light therapy lamps, xenon flash lamps, carbon arc lamps, ceramic discharge metal halide lamps, hydrargyrum medium-arc iodide lamps, mercury-vapor lamps, and metal halide lamps.

The methods and devices of the various embodiments can employed in conjunction with all suitable types of light therapy falling within the UV to IR wavelength ranges (e.g. phototherapy, bright light therapy, light therapy lamps and rooms, ocular light therapy, intracranial nerve optic therapy, ultraviolet phototherapy, photopheresis, extracorporeal photochemotherapy, photodynamic therapy, etc.). The various embodiments in combination with light therapy can improve depression outcomes, and improve overall well-being in patients.

One embodiment includes identifying a patient's resonance frequency through EKG, HRV-HR monitor, HRV-HR watch, HRV-HR video capture, radar, or Doppler means, and to then automatically or manually trigger a pattern of light stimulation to induce resonance for the patient. Another embodiment employs other metrics such as galvanic skin response to measure sympathetic activity or muscle tension to trigger appropriate light stimulation. Other sensed physiological parameters are also contemplated to trigger light stimulation. In yet another embodiment, automated stimulation cycles having 11 second third periods are employed to trigger oscillations close to a patient's resonance frequency.

The resonance or high amplitude oscillations induced or created by the methods described and disclosed herein may be used to treat a patient for a stress-related disorder, depression, hypertension, an autonomic dysfunction, atrial fibrillation, coronary heart disease, diabetes, post-traumatic stress disorder, substance abuse, and yet other disorders, maladies or diseases. Such induced or created resonance, or forced oscillations, can also be employed to increase a patient's baroreflexes, increase the flexibility of a patient's CVS, and/or increase or improve a patient's vagal nerve tone and/or stress reactivity.

Successive cycles comprising the first and second periods may then be repeated as long as desired to effect suitable entrainment of the CVS. Successive cycles can also be terminated, adjusted or modified in accordance with physiological parameters of the patient that have been sensed.

The above described embodiments should be considered as examples of the present invention, rather than as limiting the scope of the invention. In addition to the foregoing embodiments of the invention, review of the detailed description and accompanying drawings will show that there are other embodiments of the present invention. Accordingly, many combinations, permutations, variations and modifications of the foregoing embodiments of the present invention not set forth explicitly herein will nevertheless fall within the scope of the present invention.

The invention claimed is:

1. A method of providing light stimulation therapy to a patient, comprising:

identifying a resonance frequency of a cardiovascular system associated with the patient;

selecting signal parameters for a light stimulation signal based on the resonance frequency of the cardiovascular system associated with the patient, wherein the signal parameters include a first time period associated with a first type of light stimulation signal, a second time period associated with a second type of light stimulation signal, and a third period that is equivalent to a combination of the first time period and the second time period and that is also equivalent to the resonance frequency of the cardiovascular system of the patient; and delivering, using a device capable of configuring light to create the first type of light stimulation signal for the first time period and the second type of light stimulation signal for the second time period, the light stimulation signal to the patient, wherein the light stimulation signal includes the first type of the light stimulation signal being successively delivered to the patient over the first time period and a second type of the light stimulation signal being delivered to the patient over the second time period, the second time period being interposed between instances of the first time period.

2. The method of claim 1, wherein the first time period is adjacent to the second time period.

3. The method of claim 1, wherein the third period of time ranges between about 8 seconds and about 14 seconds.

4. The method of claim 1, wherein the third period of time ranges between about 26 seconds and about 34 seconds.

5. The method of claim 1, wherein the first period of time ranges between about 4 seconds and about 7 seconds.

6. The method of claim 1, wherein the second period of time ranges between about 4 seconds and about 7 seconds.

7. The method of claim 1, wherein the first period of time ranges between about 13 seconds and about 17 seconds.

8. The method of claim 1, wherein the second period of time ranges between about 13 seconds and about 17 seconds.

9. The method of claim 1, wherein an electromagnetic wavelength of the light stimulation signal is in a range between 100 nm to 1 mm.

10. The method of claim 1, wherein the light stimulation signal has wavelengths ranging between about 380 nm and about 710 nm.

11. The method of claim 1, wherein the light stimulation signal has a substantially uniform wavelength during active light stimulation.

12. The method of claim 1, wherein the light stimulation signal has a substantially uniform intensity during active light stimulation.

13. The method of claim 1, wherein an intensity of the light stimulation signal is modified during active light stimulation.

14. The method of claim 1, wherein the first type of light stimulation signal corresponds to an "on" mode in which the light stimulation signal is being delivered to the patient, and wherein the second type of light stimulation signal corresponds to an "off" mode in which the light stimulation signal is not being delivered to the patient.

15. The method of claim 1, further comprising sensing a physiological parameter of the patient and, in response to such sensing, adjusting the third period.

16. The method of claim 1, wherein the resonance frequency of the cardiovascular system associated with the patient is determined based on a height and a gender of the patient.

17. The method of claim 1, wherein the resonance frequency of the cardiovascular system associated with the patient is less than about 0.125 Hz.

18. The method of claim 1, wherein the first type of light stimulation signal and the second type of light stimulation signal are delivered using a light source.

19. The method of claim 18, wherein the light source is a light bulb.

20. The method of claim 18, wherein the light source is a display of a computing device and wherein the method further comprises configuring the display of the computing device to modify a brightness of the display during active light stimulation.

\* \* \* \* \*